United States Patent [19]

Parent

[11] 4,441,501

[45] Apr. 10, 1984

[54] MEDICAL ELECTRODE

[75] Inventor: James R. Parent, Dayton, Ohio

[73] Assignee: NDM Corporation, Dayton, Ohio

[21] Appl. No.: 356,096

[22] Filed: Mar. 8, 1982

[51] Int. Cl.³ .............................................. A61B 5/04
[52] U.S. Cl. ..................................... 128/641; 128/803
[58] Field of Search ............................. 128/639–641, 128/643, 644, 798, 802, 803, 303.13

[56] References Cited

U.S. PATENT DOCUMENTS

| | | | |
|---|---|---|---|
| 3,085,577 | 4/1963 | Berman et al. | 128/641 |
| 3,696,807 | 10/1972 | Szpur | 128/641 |
| 3,701,346 | 10/1972 | Patrick et al. | 128/641 |
| 3,713,435 | 1/1973 | Szpur | 128/641 |
| 3,820,531 | 6/1974 | Szpur | 128/641 |
| 3,830,229 | 8/1974 | Johnson | 128/641 |
| 3,841,312 | 10/1974 | Corasanti | 128/641 |
| 3,848,600 | 10/1983 | Patrick et al. | 128/303.13 |
| 3,895,635 | 7/1975 | Justus et al. | 128/303.13 |
| 3,942,517 | 3/1976 | Bowles et al. | 128/641 |
| 3,982,529 | 9/1976 | Sato | 128/641 |
| 3,989,035 | 11/1976 | Zuehlsdorff | 128/641 |
| 4,019,500 | 4/1977 | Patrick, Jr. et al. | 128/641 |
| 4,029,086 | 6/1977 | Corasanti | 128/641 |
| 4,040,412 | 8/1977 | Sato | 128/640 |
| 4,114,263 | 9/1978 | Szpur | 29/641 |
| 4,137,909 | 2/1979 | Hix | 128/641 |
| 4,161,174 | 7/1979 | Mercuri | 128/641 |
| 4,226,247 | 10/1980 | Hauser et al. | 128/641 |

Primary Examiner—Lee S. Cohen
Attorney, Agent, or Firm—Dybvig & Dybvig

[57] ABSTRACT

The eyelet of a snap fastener conductor extends both through an adhesively coated supporting sheet and a gel pad whereupon a flange on the eyelet cooperates with the gel pad to form a cuplike cavity in which electrolyte gel is placed. The supporting sheet is formed from a substantially moisture and water vapor impervious material and cooperates with a cover that is also substantially moisture and water vapor impervious having a cavity receiving the gel pad to prevent gel dry out.

9 Claims, 4 Drawing Figures

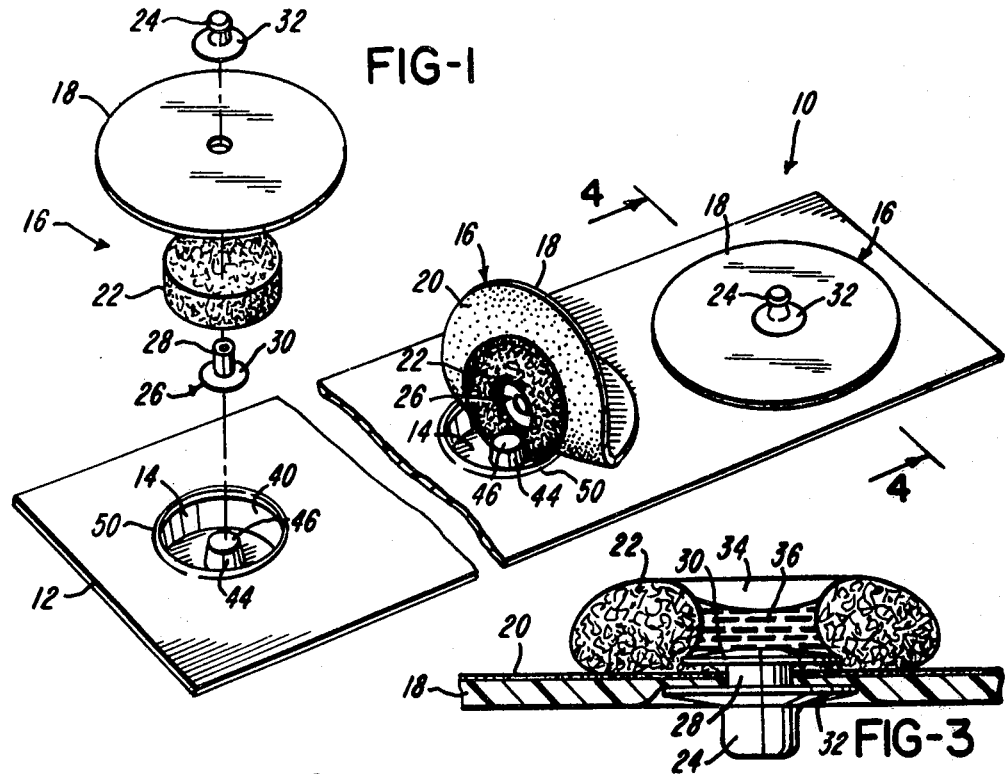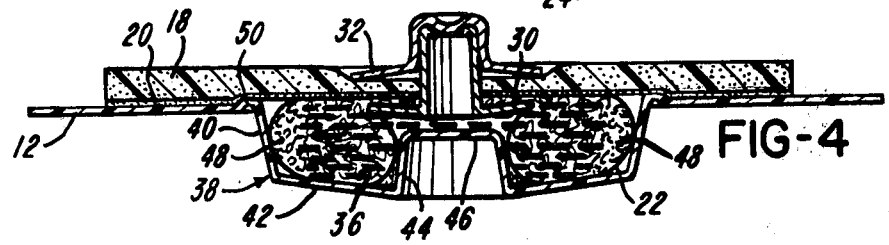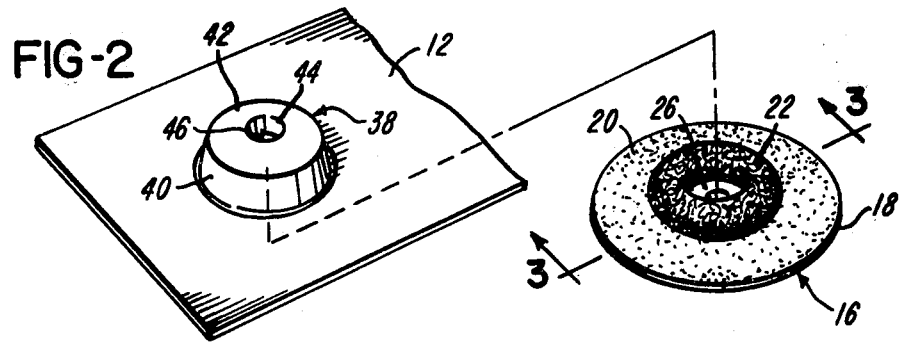

MEDICAL ELECTRODE

SUMMARY OF THE INVENTION

This invention relates to a medical electrode and primarily to a medical electrode for use in EKG testing procedures, although aspects of the invention may also be used in medical electrodes generally for establishing an electrical connection between the skin of an animal, usually a human, and signal monitoring or signal applying devices of various types.

The invention is primarily directed to improvements in disposable, low-profile electrodes, that is, electrodes which has a relatively low height with respect to area of skin contact. In particular, the electrodes are of a type including an adhesively coated sheet for engaging the skin, an electrode conductor supported by the sheet, an electrolyte in the form of a gel for transmitting electrical signals between the conductor and the skin, and a foam gel pad loaded with the electrolyte. The primary purpose of the gel pad is to promote stability in the functioning of the electrolyte by insuring reasonably uniform and constant contact between the electrolyte and both the electrode conductor and the skin. The electrodes are known as "pre-filled" because the gel pad is filled with an electrolytic jelly during manufacture whereby the electrode is ready for immediate use as soon as it is unpackaged.

The electrodes of this invention are primarily intended for use in relatively short-term EKG testing in medical laboratories or doctor's offices. A common procedure involves the use of two sets of five electrodes each, or a total of ten electrodes, and if such electrodes are to be disposable, each electrode must be economically manufactured.

In a modification, an improved electrode is provided which may be used for ECG monitoring during surgery.

Many medical electrodes presently in use include an adhesively coated, skin contacting supporting sheet having a conductor in the form of a snap fastener element projecting through the supporting sheet and also through a relatively rigid cup member. The cup member, known as a "gel cup," engages the adhesive coating on the supporting sheet and receives a gel pad loaded with an electrolyte. One of the functions of the gel cup is to confine the gel pad and the electrolytic gel to optimize the signal handling characteristics of the electrode by insuring good stable contact at all times between the electrolyte and both the conductor and the skin. Also, it is important to confine the gel so that it does not squeeze out substantially beyond the margins of the gel cup and engage the adhesive coating on the supporting sheet and thereby interfere with the engagement between the adhesive coating and the skin. The gel cup in many electrodes cooperates with a cover structure to house the gel pad in a sufficiently water and air-tight chamber to prevent the gel pad from drying out over a prolonged period of time.

Considerable care must be taken when assembling electrodes having a gel cup and a gel pad received by the gel cup. In some cases, the gel pad is loaded with an electrolytic jelly prior to being placed in the gel cup, and the placement of the gel pad is done manually. In order to minimize the expense of manufacture, it is important to avoid manual operations. Therefore, an alternative procedure is to first place the gel pad into the gel cup and then load it with an electrolyte by injecting the electrolytic jelly into the gel pad. It is necessary in this practice to apply pressure to the gel pad while the jelly is being injected into the pad, as by having the nozzle firmly engaged with the pad. The jelly must be injected under substantial pressure to insure that it is dispersed throughout the pad. As a practical matter, it is not possible to apply uniform amounts of jelly so that occasionally there may be either too much or too little jelly applied to the pad.

Another problem with medical electrodes having a gel cup with a gel pad is that the gel pad may fall out of the gel cup just as the electrode is about to be applied to the skin of a patient. Replacement of the gel pad would render use of that particular medical electrode unsanitary. Various means such as adhesives or parts mechanically engaging the gel pad have been used, but without complete satisfaction.

An object of this invention is to provide an improved, low cost, disposable, low profile, pre-filled medical electrode.

It is a further object of this invention is to improve upon existing medical electrode constructions by providing a medical electrode in which a gel pad is securely affixed to an adhesive supporting sheet by an electrode conductor which extends substantially centrally through the gel pad and to form the electrode conductor and the gel pad such that they cooperate to form a cuplike cavity for receiving the electrolytic gel. Accordingly, a separate gel cup is not needed. The gel can be added to the electrode during manufacture simply by injecting the gel into the cuplike cavity. The gel spreads to portions of the gel pad surrounding the cavity and part of the gel remains in the cavity. Accordingly, the need for highly accurate control of the amount of gel that is used in manufacturing the electrode or the manner of application is minimized. Further, it has been found through tests that the gel typically does not completely fill the gel pad in surrounding relation to the cuplike cavity and therefore does not migrate to the portion of the adhesive coating that is to be applied to the skin. The pressure exerted on the electrode as it is applied to the skin causes the electrolyte to more completely fill the gel pad. Also, the pressure applied to the gel pad partially collapses the gel pad and accordingly, reduces the depth of the cuplike cavity which is thereby completely filled with gel. As a result of the filling of the cavity and of the gel pad with gel, good electrical contact is assured at all times between the skin and the conductor through the electrolyte.

The gel pad is preferably made from a material known as a fully reticulated polyurethane foam, which is an open cell foam material. In accordance with this invention, the central portion of the gel pad is tightly squeezed against the adhesive layer on the supporting sheet by the electrode conductor. It is found that, if the gel pad is made in the form of a generally cylindrical disc, the portion of the gel pad surrounding the electrode conductor will become curved and, at the same time, expand in width, apparently as a result of the squeezing forces applied to the center portion of the pad. Accordingly, the pad forms a soft cup wall partly covering the margins of the electrode conductor and thereby it is assured that the electrode conductor will not engage the skin. A soft cup wall is an advantage in that the electrodes are relatively comfortable when applied to the skin.

To minimize cost, the snap fastener elements are preferably made from stainless steel, such being entirely satisfactory for short term EKG use. In a modification, the snap fastener parts may be made from silver or silver plated plastic parts for use in ECG monitoring in operating rooms.

The supporting sheet is preferably moisture and water vapor impervious, at least adjacent the gel pad, and a suitable cover or backing strip is provided to minimize gel dry out. A closed cell polyethyelene foam supporting sheet is preferred because such material is inexpensive and easy to handle during manufacture. The cover or backing strip may be, as conventional, made from a vacuum formed styrene or other suitable moisture and water vapor impervious plastic material.

Other objects and advantages of this invention will be apparent from the following description.

BRIEF DESCRIPTION OF THE DRAWING

FIG. 1 is a perspective view taken generally from the top of an electrode assembly including at least three medical electrodes with one of the electrodes shown in exploded view and exploded from a backing sheet, another of the electrodes shown partly removed from the backing sheet, and the third electrode shown in assembled position on the backing sheet as it would appear following manufacture and during shipping and storage. The gel is not shown in FIG. 1.

FIG. 2 is a perspective view of a portion of the electrode assembly of FIG. 1 and illustrating one of the medical electrodes which is shown exploded from the backing sheet and as viewed from the bottom of the backing sheet and the electrode. The gel is also not shown in FIG. 2.

FIG. 3 is a fragmentary cross-sectional view of the medical electrode shown in FIG. 2 taken along section line 3—3 thereof and showing the electrolytic gel as it would appear shortly after it is added during manufacture.

FIG. 4 is a cross-sectional view of the assembled electrode and the backing sheet taken along line 4—4 of FIG. 1 and indicating, by heavy dash lines, the location of the gel following final assembly.

DETAILED DESCRIPTION OF THE PREFERRED EMBODIMENTS

With reference to the drawing, a medical electrode assembly in accordance with this invention is generally designated 10 and includes an elongate cover or backing strip 12 having plural, upwardly opening cavities 14, one for each of a plurality of medical electrodes that are generally designated 16. There may be any number of medical electrodes 16 forming part of the assembly 10. Often, an assembly 10 would have five electrodes and would be packaged in a suitable pouch (not shown) with a second, identical electrode assembly, such being the common practice for relatively short term laboratory EKG use.

Each medical electrode 16 comprises a body member in the form of an adhesive pad or supporting sheet 18 rendered adhesive by a layer 20 of adhesive completely coating its bottom surface. The adhesive sheet 18 is centered coaxially with the cavity 14 that it overlies. Each electrode 16 further includes, in coaxial alignment with the adhesive sheet 18, a gel pad 22, an electrically conductive snap fastener stud 24, and an electrically conductive snap fastener eyelet 26 having a shank 28 pierced substantially through the center of the gel pad 22 and the supporting sheet 18. The eyelet 26 further includes a circular base flange 30 projecting from the bottom of the shank 28. When the parts are assembled, the eyelet flange 30 confronts a flange 32 forming part of the stud 24. Following conventional practice, the stud 24 and the eyelet are riveted together so that the stud 24 forms a knob suitable for attachment to a lead wire (not shown). In accordance with this invention, the stud flange 32 and the eyelet flange 30 also tightly squeeze the central portions of the adhesively coated supporting sheet 18 and the gel pad 22 therebetween.

By virtue of the fact that the center portion of the gel pad 22 is tightly squeezed against the supporting sheet 18, and because the center portion of the gel pad 22 is thus substantially reduced in thickness, a cuplike cavity 34 is produced that has a cup wall formed by the portion of the gel pad 22 encircling the eyelet flange 30, and a cup base formed by the exposed face of the eyelet flange 30.

After the parts as thus far described are assembled, an electrolyte gel 36, illustrated in FIG. 3, is added. The gel 36 may simply be inserted through a nozzle (not shown) centered over the cavity 34 while the electrode is inverted as shown in FIG. 3. The gel then migrates into portions of the gel pad 22 surrounding the gel receiving cavity 34.

The backing sheet 12 may be made from a variety of plastic materials suitable to be manufactured by thermovacuum forming or other inexpensive manufacturing techniques. It is preferably made from styrene or other plastic material that is relatively stiff in a thin section and substantially impervious to moisture and water vapor.

It is within the purview of this invention that the cavities 14 may take a variety of different shapes suitable to providing a housing for the gel pad 22 and the gel 36. The presently preferred shape, which was designed by a fellow worker, is illustrated best in FIGS. 2 and 4, and is formed by a protuberance generally designated 38 in the form of a truncated cone having a generally circular outer wall 40, an arcuate bottom wall 42 that curves convexly downwardly, and a centrally formed cavity plug 44 having a center base portion 46 projecting from the bottom wall 42 toward the plane containing the major portion of the backing sheet 12 so that, as shown in FIG. 4, when the parts are assembled, the base 46 of the cavity plug 44 confronts and is slightly spaced from the eyelet flange 30. The protuberance 38 is formed to be of a size to be substantially filled by the gel pad 22, and in fact, may slightly compress part of the gel pad 22. The cavity plug portion 44 is also in the form of a truncated cone, and is sized to substantially match the diameter of the gel receiving cavity 34. As the parts are assembled, the cavity plug 44 will force gel outwardly into the gel pad 22 and ultimately the gel 36 will migrate throughout a substantial portion of the pad 22 as indicated by the heavy dash lines in FIG. 4. However, because the gel pad foam material provides a substantial resistance to migration of the gel, the gel typically does not migrate to the outer peripheral portions 48 of the pad 22. It may also be noted that the size of the protuberance 38 is such that its maximum diameter is only slightly greater than the diameter of the gel pad 22 so that the surrounding portions of the adhesive coating 20 are engaged with the top surface of the backing sheet 12 surrounding the cavity 14. Preferably, this top surface has a silicon release coating so that the medical electrode may be easily removed therefrom as illustrated in FIG. 1. Partly because of the engagement between the adhesive coating 20 and the top surface of the backing sheet 12, and also because the gel does not migrate to the outer margins of the gel pad 22, the gel pad 22 itself forms a barrier to migration of the gel 36 to the adhesive layer 20 surrounding the gel pad 22. As a further precaution against migration of the gel 36, the backing sheet 12 may be formed with raised lips 50 at the margins of the cavities 14 to promote a good seal around the cavities 14 between the backing sheet 12 and the supporting sheet 18.

It is common practice for those using medical electrodes such as the electrode 16 to apply lead wires to all of the electrodes before they are removed from the backing sheet 12. An advantage of the construction of the protuberance 38, and particularly the manner in which the cavity plug 44 is formed, is that, when one is connecting a lead wire having a snap-on connector by pressing downwardly, the eyelet flange 38 engages the base 46 of the cavity plug 44 which thus prevents the gel pad 22 from being collapsed. Thus, a condition which might cause the gel 36 to be squeezed onto the surrounding areas of the adhesive layer 20 is avoided.

The adhesively coated supporting sheet 18 may be formed from a variety of thin, flexible plastic materials provided that they are substantially impervious to moisture and water vapor. The presently preferred material is a closed cell polyethelene foam which is inexpensive and readily available. Vinly or other materials could also be used. In any case, the material must be substantially moisture and water vapor impervious so that it can cooperate with the backing sheet 12 to form a moisture retaining chamber for the gel pad 22 to prevent the gel 36 from drying out. As an option, the parts of the supporting sheet 18 secured to the backing sheet 12 could have perforations (not shown) extending therethrough. Such perforations would allow the adhesively engaged portions of the skin to 37 breathe."

The adhesive 20 may be any suitable adhesive for adhering the electrode to the skin, there being many such adhesives well known to those familiar with the manufacture of medical electrodes. A medical grade acrylic adhesive is presently preferred, but various other compositions may be used with equivalent results.

The gel pad 22 is preferably a sponge made from a highly open cell, fully reticulated polyurethane foam. This material has both resiliency and flexibility and is commonly used in the manufacture of medical electrodes. However, there may be other open cell materials which could be used. The pad 22 is initially formed as a circular disc as shown on the left side of the FIG. 1. It is sized such that its outer margins are spaced inwardly from the outer margins of the supporting sheet 18, whereupon it leaves exposed a sufficiently large surface area of the adhesive coating 20 to reliably secure the electrode to the skin of a patient.

When the gel pads 22 are squeezed by the snap fastener parts during assembly, the pads 22 become rounded as shown best in FIG. 3. Furthermore, the squeezing of the center portion of the gel pad 22 causes the immediately surrounding portions to expand to a greater thickness than the original pad 22 by approximately 25 percent so as to increase the depth of the gel receiving cavity 34. Also, as illustrated in FIGS. 3 and 4, the surrounding portions of the gel pad 22 bulge or become rounded in a fashion to overlie the outer margin of the eyelet flange 30.

When the electrode is applied to the skin, the gel pad 22 is partly collapsed. The cavity 34, although reduced in size, still exists and there is an assured separation between the skin and the eyelet flange 30, such separation being considered desirable in a medical electrode as well known to those familiar with the art. However, the partly collapsed gel pad 22 still retains the electrolyte gel 36 and there is also gel 36 filling the cavity 34 so that a good, stable contact is provided between the skin and the eyelet flange 30. Furthermore, it is found that the gel 36 does not migrate to the adhesive layer 28 to interfere with the adhesion of the electrode to the skin. This is believed due in part to the fact that the gel pad 22 is not fully loaded with the gel 36. Accordingly, as the gel pad 22 is partly collapsed when the electrode 16 is applied to the skin, the gel 36 may be squeezed into the part 48 of the gel pad 22 not previously loaded with gel, but the gel is not squeezed out beyond the margins of the gel pad 22. Avoidance of fully loading the gel pad 22 with gel 36 during manufacture provides another advantage in that the amount of gel that is used in the manufacture of each electrode is not critically important. Furthermore, it is an advantage that the gel can simply be deposited in the gel receiving cavity 34 from whence it migrates into the gel pad 22.

The stud 24 and the eyelet 26 are preferably made from like conductive elements. For use in EKG monitoring, the stud 24 and the eyelet 26 may be made from stainless steel, stainless steel being inexpensive, strong, and easily formed during manufacture. The stud and the eyelet should be made from the same metal because there is a liklihood that some of the electrolytic gel 36 will be forced centrally through the eyelet shaft 28 or else will migrate around the outside of the eyelet shaft 28 into engagement with the stud 24 and, as those familiar with the art are aware, it is undesirable to have the electrolyte engage dissimilar metals. Stainless steel may be unsatisfactory for some uses, such as in an operating room, in which case the stud and the eyelet are preferably made from silver or silver-plated plastic.

Preferably the eyelet flange 30 is circular. In any case, it must be dimensioned to have a surface area sufficiently smaller than the pad 22 so that the outer margin of the pad 22 forms the cup wall as described above when the center portion of the gel pad 22 is squeezed against and thereby held in fixed relation to the adhesive supporting sheet 18.

The gel may be made from any composition compatible with the conductive material from which the eyelet 26 is manufactured, a non-chloride composition being used in the event the eyelet is made from stainless steel and a chloride composition being used in the event the eyelet is made from silver. Again, the selection of the composition is not critical to this invention, and any of several compositions known to those familiar with the art may be used.

It will be appreciated that this invention provides a low cost medical electrode made from a minimum number of parts. Particularly, many of the advantages of an electrode having a gel cup are obtained but without the use of a gel cup by utilizing the eyelet flange both as the electrolyte engaging conductor and also as a device to squeeze the center portion of the gel pad against the adhesively coated supporting sheet. By forming the cover or backing strip 12 with the cavities 14 for receiving the gel pad 22, and by the use of a supporting sheet 18 formed from a closed cell foam material which is substantially moisture and water vapor impervious, no additional structure is required to prevent the gel from drying out during ordinary periods of use after they are removed from their packaging.

Although the presently preferred embodiment of this invention has been described, it will be understood that various changes may be made within the scope of the appended claims.

Having thus described my invention, I claim:

1. A medical electrode of the type adapted to be adhered to the skin comprising:
   a flexible supporting sheet coated with adhesive on one side for adhesion to the skin of a patient and comprising a material which is substantially impervious to moisture and water vapor;
   an electrically conducting connector abutting said sheet on the side thereof opposite said one side for connection to external equipment;
   a gel pad engaging said adhesively coated surface of said sheet comprising a foam sponge having its outer margins spaced inwardly from the outer margins of said adhesively coated surface of said sheet;
   an electrolyte engaging conductor engaged with said gel pad having a first portion having one surface facing the same direction as said adhesively coated surface and an opposite surface facing toward said adhesively coated surface, having a second portion integral with the first portion extending through said gel pad and through said sheet into engagement with said connector, a portion of said gel pad being squeezed between said first portion of said conductor and said adhesively coated surface, the outer margin of said first portion being spaced inwardly from the outer margin of said gel pad so that only a portion of said gel pad is squeezed between said first portion and said adhesively coated surface, the portions of said gel pad surrounding said first portion of said conductor projecting substantially further from said adhesively coated surface than said first portion of said conductor and forming with said first portion of said conductor a cup-like cavity; and
   an electrolyte gel within said cavity and at least partially filling said gel pad.

2. The medical electrode of claim 1 wherein said gel pad and said first portion of said conductor are each generally circular and coaxially aligned.

3. The medical electrode of claim 1 or 2 further including a cover attached to said sheet and having a cavity receiving said gel pad.

4. An inexpensive disposable medical electrode comprising:
   a sheet of substantially moisture and water vapor impervious flexible material coated with an adhesive on one surface;
   a gel pad abutting said one surface;
   a snap fastener conductor comprising an eyelet extending through said gel pad and said sheet and a stud clenched to said eyelet and engaging the surface of said sheet opposite said adhesively coated surface, said eyelet including a flange portion engaging said gel pad, part of said gel pad being confined between said flange portion and said sheet, and surrounding portions of said gel pad forming with said flange portion a cavity opening in the direction that said adhesively coated surface faces; and
   an electrolyte gel within said cavity and partly filling said gel pad.

5. The medical electrode of claim 4 wherein said gel pad and said flange portion are each generally circular and coaxially aligned.

6. The medical electrode of claim 4 or 5 further including a cover attached to said sheet having a cavity receiving said gel pad.

7. In a medical electrode of the type comprising a thin flexible body member coated with adhesive on one side for adhesion to the skin of a patient, a gel pad, and a snap fastener comprising a first conductive member projecting through said body member and including an electrolyte engaging surface on the same side of said body member as said adhesive, and a second conductive member engaging said first conductive member and providing a connector for engagement to external equipment on the other side of said body member, the improvement wherein:
   said first conductive member projects also through said gel pad and includes means squeezing a portion of said gel pad against said adhesively coated one side of said body member whereupon the portion of said gel pad surrounding said squeezing means cooperates with said squeezing means to form a cavity opening in the direction that said adhesively coated surface faces, and wherein an electrolyte gel is located in said cavity.

8. The improvement of claim 7 wherein said gel pad and said squeezing means are both generally circular and coaxially aligned.

9. The improvement of claim 7 or 8 further including a cover engaging said adhesive and having a cavity receiving said pad.

* * * * *